(12) United States Patent
Pivovarov

(10) Patent No.: US 7,137,393 B2
(45) Date of Patent: Nov. 21, 2006

(54) BREATHING NORMALIZER APPARATUS

(76) Inventor: Alexander R. Pivovarov, 27 NW. 45th Ave., #208, Deerfield Beach, FL (US) 33442

( * ) Notice: Subject to any disclaimer, the term of this patent is extended or adjusted under 35 U.S.C. 154(b) by 0 days.

(21) Appl. No.: 10/736,808

(22) Filed: Dec. 15, 2003

(65) Prior Publication Data
US 2004/0211430 A1    Oct. 28, 2004

Related U.S. Application Data

(63) Continuation-in-part of application No. 10/424,680, filed on Apr. 28, 2003, now Pat. No. 6,675,804.

(51) Int. Cl.
*A61F 5/56* (2006.01)
(52) U.S. Cl. .................. 128/848; 128/859; 128/860
(58) Field of Classification Search ................ 128/848, 128/859–862, 846; 602/902, 912; 433/6
See application file for complete search history.

(56) References Cited

U.S. PATENT DOCUMENTS

| | | | | |
|---|---|---|---|---|
| 3,139,088 A | * | 6/1964 | Galleher, Jr. ........... | 128/206.29 |
| 3,692,025 A | * | 9/1972 | Greenberg ............... | 128/857 |
| 4,270,531 A | * | 6/1981 | Blachly et al. ......... | 128/207.14 |
| 5,253,658 A | * | 10/1993 | King ....................... | 128/859 |
| 5,533,523 A | * | 7/1996 | Bass et al. ............... | 128/859 |
| 6,607,382 B1 | * | 8/2003 | Kuo et al. ................ | 433/6 |
| 6,619,290 B1 | | 9/2003 | Zacco | |
| 2002/0144685 A1 | * | 10/2002 | Ivanovich et al. ........... | 128/848 |

* cited by examiner

*Primary Examiner*—Michael A. Brown
(74) *Attorney, Agent, or Firm*—Mark D. Bowen, Esq.; Stearns Weaver Miller Weissler Alhadeff & Sitterson, P.A.

(57) ABSTRACT

A breathing normalizer for partial insertion within the user's mouth for normalizing breathing patters, prevention of snoring, teeth grinding, and light forms of sleep apnea is disclosed. The device includes an outer plate which is positioned external to the user's mouth when in use, an elongated hollow shaft for connecting the structure to a lip plate adapted to be received between the user's lips and teeth, and a generally C-shaped multi-lobed structure adapted for receiving the user's tongue. The device is positioned within the oral cavity of the user in an operative configuration such that the tongue is retained within the multi-lobed structure, the teeth clamp down upon the connector with the lip plate positioned between the teeth and the inner portions of the upper and lower lips. The outer plate further defines a centrally disposed chamber having an inlet tube in fluid communication with the hollow tubular connector for providing an inlet for breathing air. The inlet tube is adapted for connection to a source of gas, such as oxygen, to assist in delivering the gas to the user through the lungs. In addition, the chamber includes a threaded peripheral edge adapted for threaded engagement with a container of medicine thereby facilitating the delivery of oral medications into the user's oral cavity and preferably the delivery of oral medications below the tongue. A medicine receiving chamber is further provided to allow for medicine received therein to be dispensed and/or evaporated in the user's mouth. As a result of proper application of the apparatus breathing at night is normalized, while snoring, grinding of the teeth, and apena are prevented, and further while medications may be simultaneously delivered orally.

8 Claims, 9 Drawing Sheets

BREATHING NORMALIZER APPARATUS

CROSS REFERENCE TO RELATED APPLICATIONS

This application is a continuation-in-part of U.S. patent application Ser. No. 10/424,680, filed Apr. 28, 2003 now U.S. Pat. No. 6,675,804.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights.

BACKGROUND OF THE INVENTION

1. Field of the Invention

The present invention relates to devices for use in promoting healthy breathing while preventing snoring, teeth grinding, and light forms of sleep apnea. More particularly, the present invention relates to an apparatus worn in the mouth of a user to normalize breathing, prevent nocturnal teeth grinding

2. Description of the Background Art

Shortness of breath, heart attacks, cancer, strokes, poor sleep, sex drive, speech problems, anxiety, seizures, anger & all disease gets better or worse by how well people breathe; the quality of respiration & oxygen usage. Many people snore while sleeping. Snoring is caused by vibration of the uvula or the soft palate in the interior of the mouth when a person breathes through his/her mouth while sleeping. The act of snoring results in an irritating sound capable of disturbing sleep patterns of many, including the person snoring. In addition to the irritating snoring sound, many consider mouth breathing to be unhealthy as it contributes to dry mouth syndrome, as well as contributing to the development of gum disease.

In addition, many people are afflicted with sleep apnea. There are three types of apnea: obstructive, central, and mixed; of the three, obstructive is the most common. Despite the difference in the root cause of each type, in all three, people with untreated sleep apnea stop breathing repeatedly during their sleep, sometimes hundreds of times during the night and often for a minute or longer. Obstructive sleep apnea (OSA) is caused by a blockage of the airway, usually when the soft tissue in the rear of the throat collapses and closes during sleep. With each apnea event, the brain briefly arouses people with sleep apnea in order for them to resume breathing, but consequently sleep is extremely fragmented and of poor quality.

Sleep apnea is very common, as common as adult diabetes, and affects more than twelve million Americans, according to the National Institutes of Health. Risk factors include being male, overweight, and over the age of forty, but sleep apnea can strike anyone at any age, even children. Yet still because of the lack of awareness by the public and healthcare professionals, the vast majority remain undiagnosed and therefore untreated, despite the fact that this serious disorder can have significant consequences.

A further abnormality experienced by many during sleep relates to gritting or grinding of one's teeth, particularly during times of stress. This disorder, refereed to as bruxism, affects numerous people at one time or another. Constant gritting of the teeth can, over time, result in the wearing away of the enamel and misshapen teeth. In severe cases, grinding of the teeth can result in loose or fractured teeth.

As a result there exists a need for a mouthpiece apparatus designed to normalize breathing patterns while also being useful in the prevention and treatment of snoring, light forms of sleep apnea, and gritting of the teeth.

BRIEF SUMMARY OF THE INVENTION

The present invention provides an apparatus adapted for partial insertion within the mouth of a user to normalize breathing, to prevent snoring, teeth grinding, and light forms of sleep apnea. The apparatus comprises a mouthpiece structure for positioning and/or restraining movement of the tongue. The device includes a curved outer plate which is positioned external to the user's mouth when in use, an elongated hollow shaft for connecting the structure to a lip plate adapted to be received between the user's lips and teeth, and a generally C-shaped multi-lobed structure adapted for receiving the user's tongue. The device is positioned within the oral cavity of the user in an operative configuration such that the tongue is retained within the multi-lobed structure, the teeth clamp down upon the connector with the lip plate positioned between the teeth and the inner portions of the upper and lower lips. The outer plate further defines a centrally disposed chamber having an inlet tube in fluid communication with the hollow tubular connector for providing an inlet for breathing air, or the delivery of liquid medicine or gas. The inlet tube is adapted for connection to a source of gas, such as oxygen, to assist in delivering the gas to the user through the lungs. In addition, the chamber includes a threaded peripheral edge adapted for threaded engagement with a container of medicine thereby facilitating the delivery of oral medications into the user's oral cavity and preferably the delivery of oral medications below the tongue. As a result of proper application of the apparatus breathing at night is normalized, while snoring, grinding of the teeth, and apena are prevented, and further while medications may be simultaneously delivered orally.

Accordingly, it is an object of the present invention to provide an apparatus to normalize breathing, while further preventing snoring and grinding of the teeth during sleep.

Yet another object of the present invention is to provide an apparatus that prevents snoring while enabling the user to breathe through the mouth.

Still another object of the present invention is to provide an oral device for use in regulating breathing while further facilitating the oral delivery of medications.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

The drawings furnished herewith illustrate a preferred construction of the present invention in which the above advantages and features are clearly disclosed as well as other

DETAILED DESCRIPTION OF THE INVENTION

Figure 1:
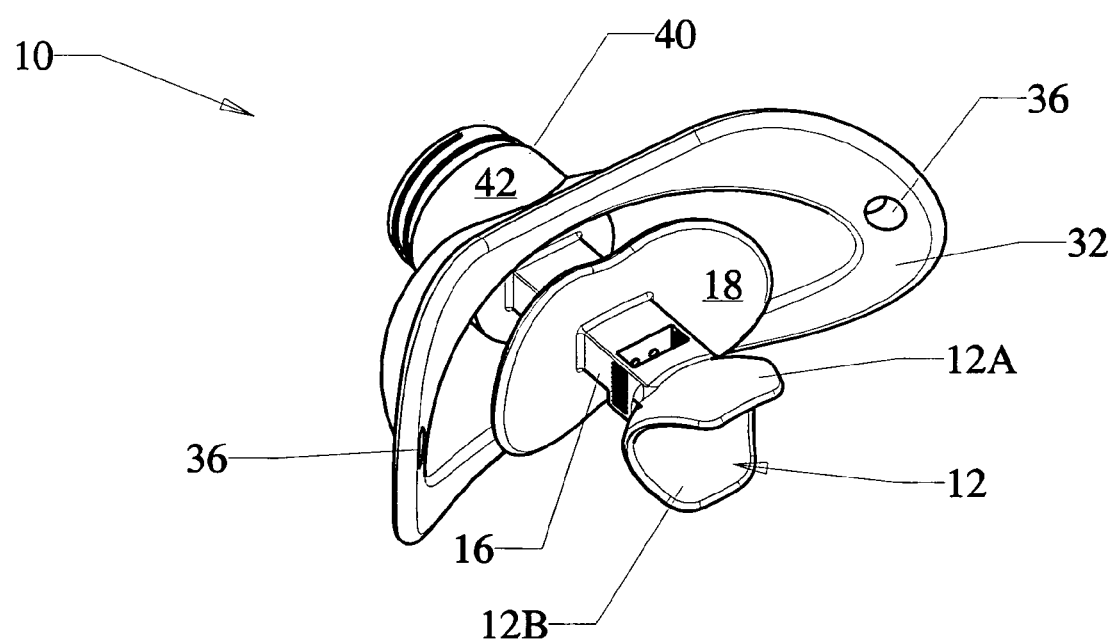
FIG. 1 is a rear perspective view of an apparatus according to the present invention.
Figure 2:
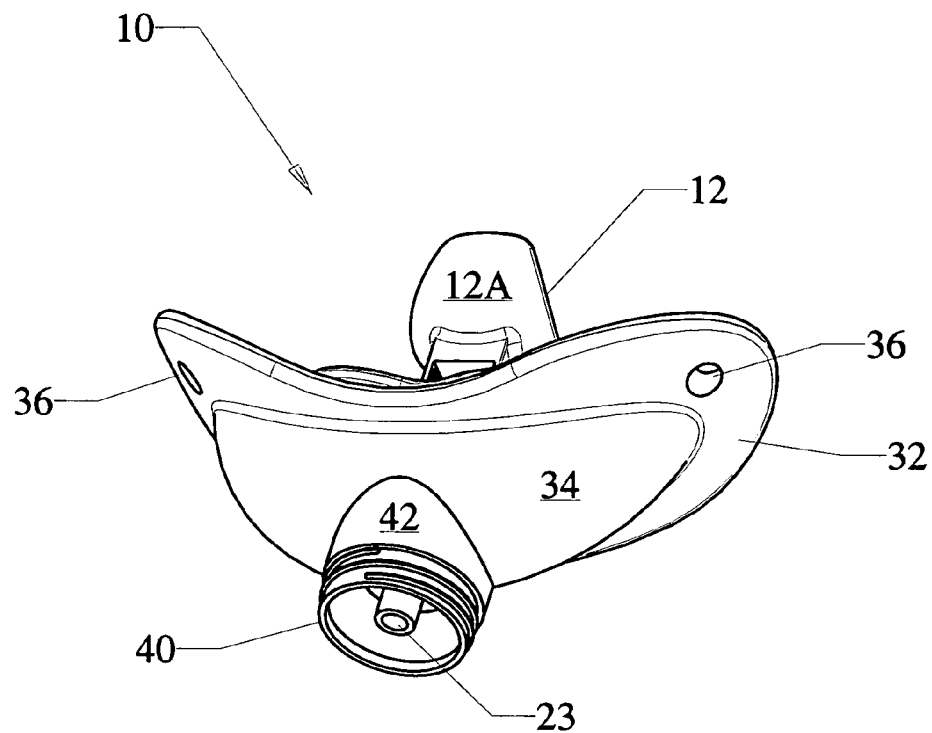
FIG. 2 is a front perspective view thereof.
Figure 3:
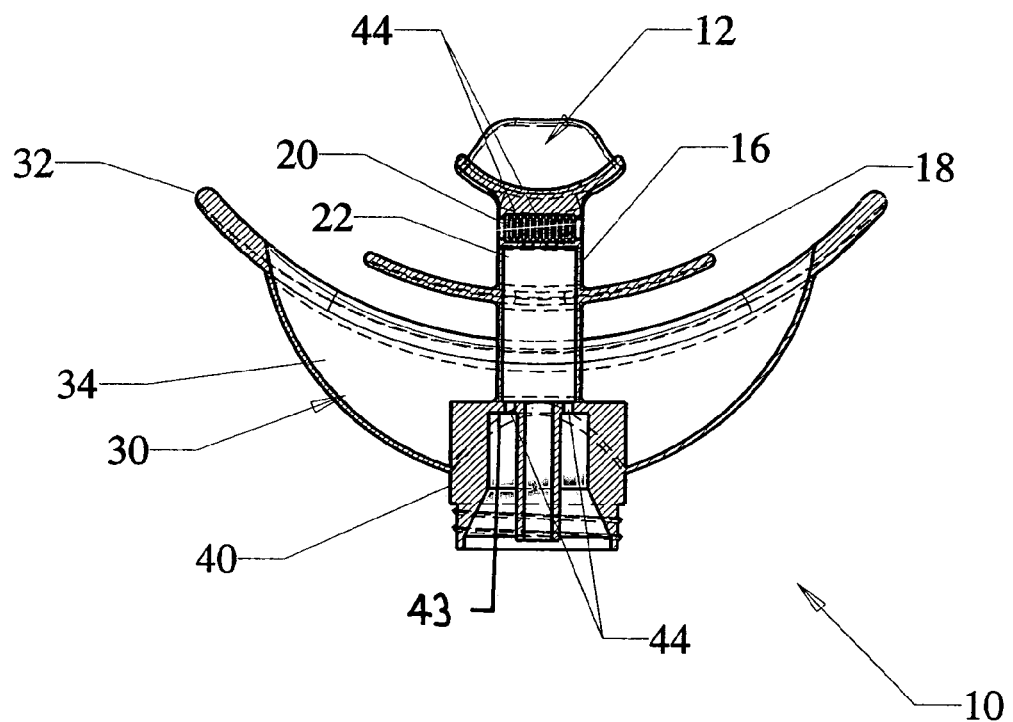
FIG. 3 is a bottom view thereof in section.
Figure 4:
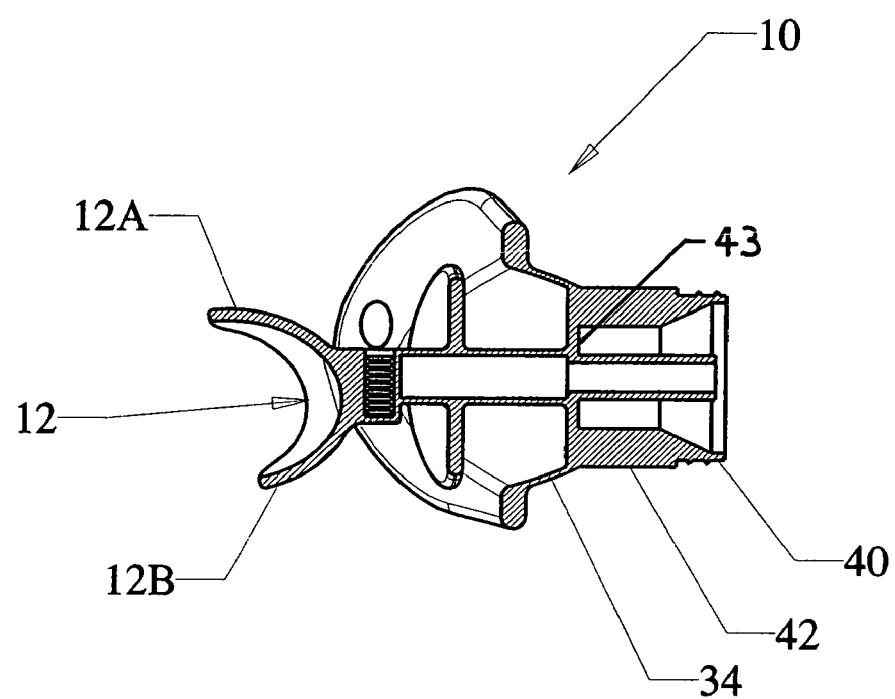
FIG. 4 is a side view thereof in section.
Figure 5:
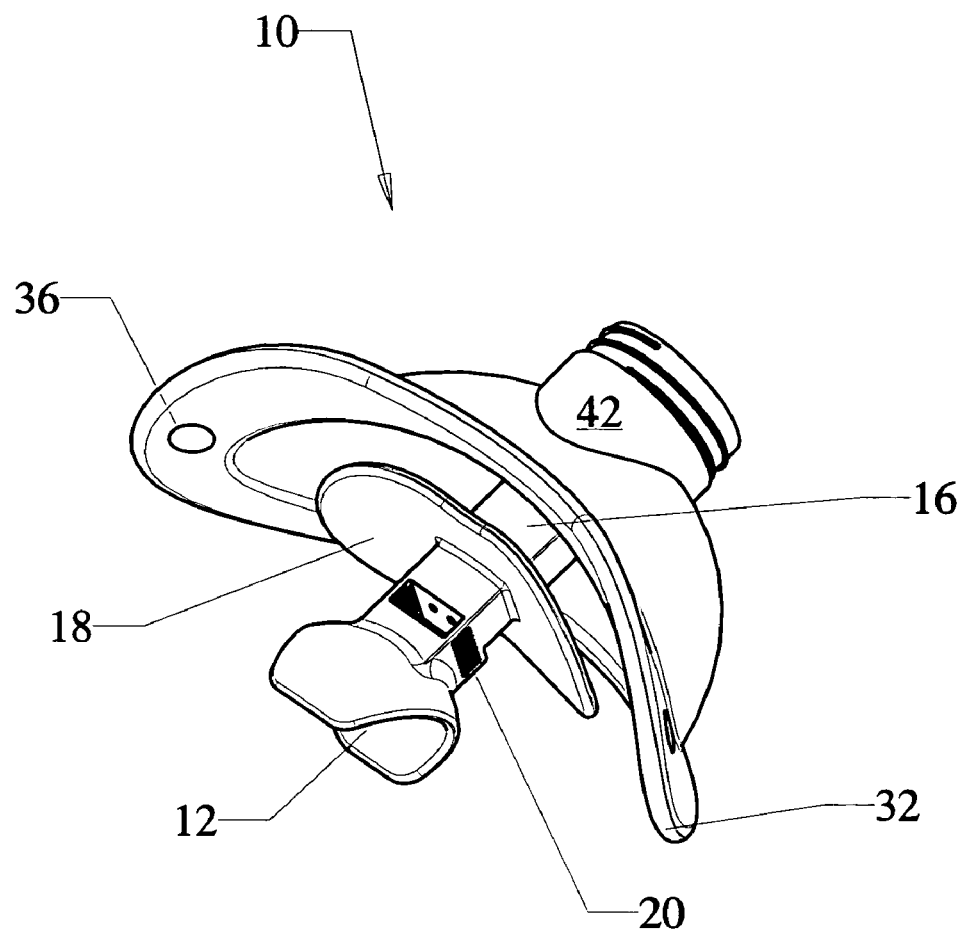
FIG. 5 is a bottom perspective view thereof.
Figure 6:
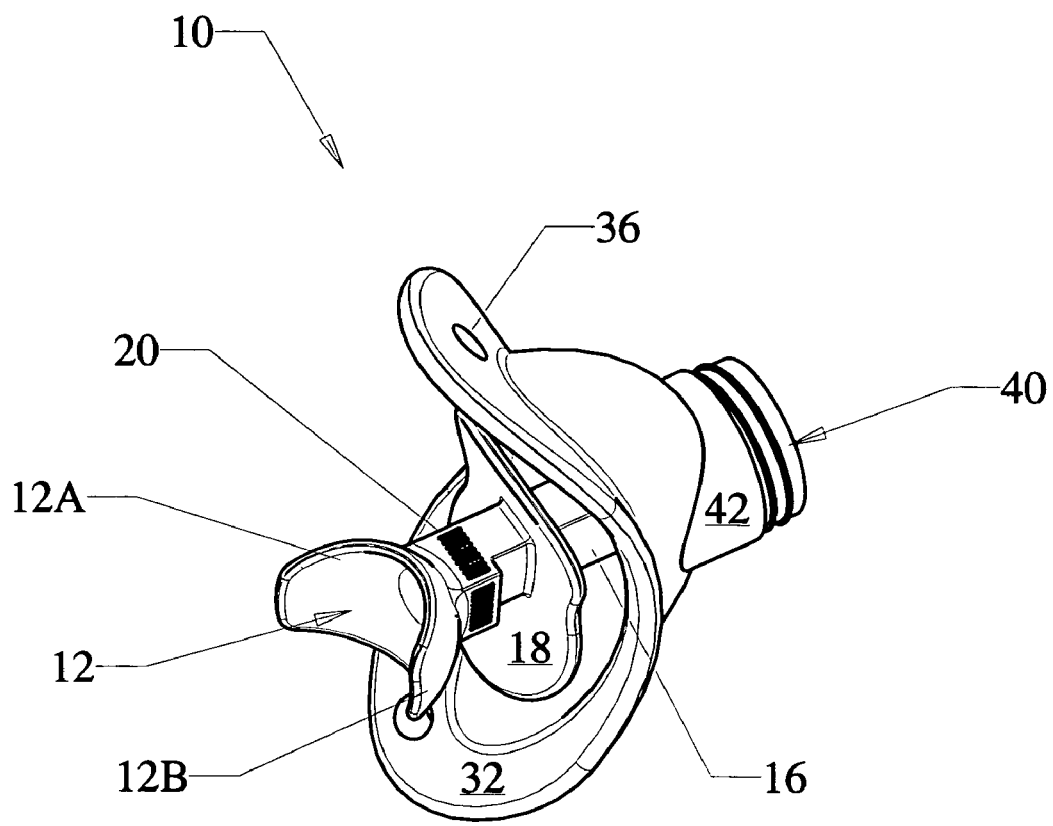
FIG. 6 is a side perspective view thereof.

Referring to FIGS. 1–9, the breathing normalizer apparatus of the present invention is generally designated by the reference numeral 10. Apparatus 10 is designed to normalize breathing for preventing snoring, teeth grinding, and/or light forms of obstructive apnea when worn by a user during periods of sleep, while being adapted to deliver medications and/or medical gases via the oral cavity. As more fully discussed herein, breathing normalizer apparatus 10 is configured as a mouthpiece, sized and shaped for so as to remain comfortably inserted within the oral cavity of the user during sleep. Breathing normalizer 10 is preferably molded from a pliable, plastic material, such as medical grade silicon material and/or other suitable plastic certified for direct contact with mucous and blood. In an alternate embodiment the material forming breathing normalizer 10 may be permanently flavored, e.g. apple, mint, bubblegum, cherry, or any other suitable flavor. In a further alternate embodiment, the material forming breathing normalizer 10 is selected from a group of material that reacts to temperature by changing color. As a result, breathing normalizer 10 may indicate to attending medical personnel whether the user's temperature is normal or elevated by color.

As discussed above, apparatus 10 is designed for positioning within the mouth of a user. The mouth includes a cavity that terminates externally at upper and lower lips, and internally at the pharynx or gullet. The mouth encloses an upper mandible having upper gums and teeth depending therefrom, and a lower mandible likewise terminating at a lower gum with lower teeth extending upwardly therefrom.

Apparatus 10 includes a tongue receiving structure 12 shaped as a semi-spherically curved oval defining vertically disposed upper and lower lobes, referenced as 12A and 12B, for positioning and/or restraining the tongue when in use. Tongue receiving structure 12 is attached to an elongate connecting shaft 16 having a first end projecting from the convex side of tongue receiving structure 12 and a flanged lip plate 18 projecting from a mid-point along the length thereof. Elongate shaft 16 defines a chamber 20 defined by walls defining a plurality of through bore apertures. In an alternate embodiment, chamber 20 may be defined by mesh walls, porous walls, or any other wall structure that permits fluid flow therethrough. Chamber 20 is adapted to receive appropriate dosages of oral medications (e.g. pill, powder, and/or liquids) therein, which medications may be dissolved by and/or evaporated into the oral cavity. Elongate shaft 16 further defines an interior bore 22 having a first end in communication with chamber 20 and a second end in communication with the atmosphere as further described herein below.

As discussed herein above, elongate shaft 16 has a flanged lip plate 18 projecting outwardly therefrom. Lip plate 18 is a generally oval flanged structure designed to fit comfortably between the user's upper and lower front teeth and lips. The second end of shaft 16 is attached to outer shield component, generally referenced as 30. Outer shield component 30 includes a first side normally disposed adjacent to the user's face defining a slightly concave peripheral edge portion, referenced as 32, in surrounding relation with a generally oval protruding central portion, referenced as 34, defining space for receiving the user's lips. Peripheral edge portion defines a pair of opposing apertures 36 which function both as ventilation ports as well as connection locations for attachment of a strap (not shown) for hanging the apparatus to dry after washing.

Figure 7:
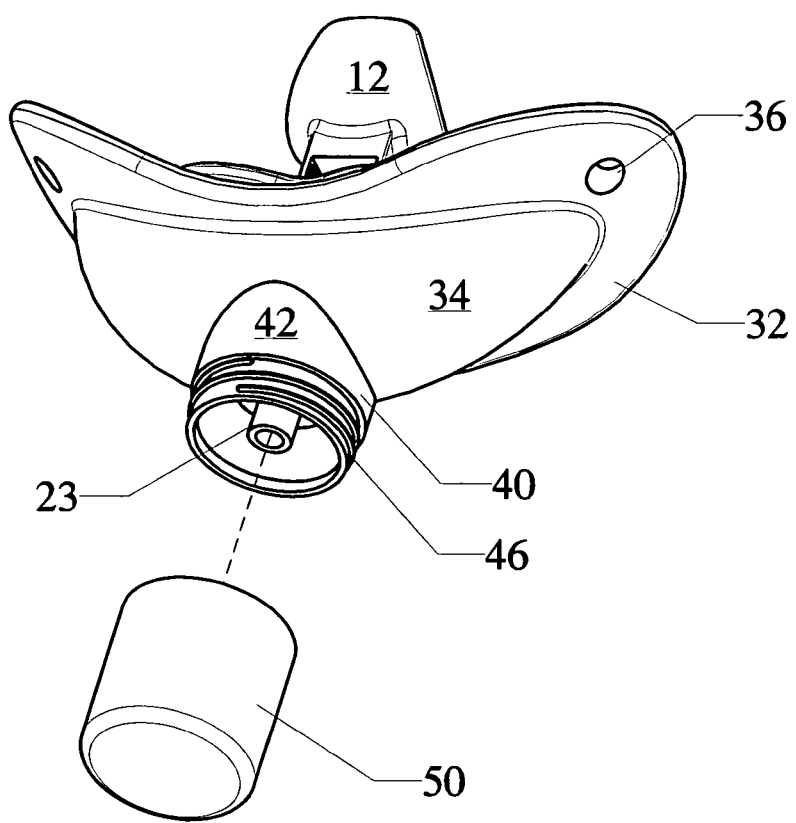
FIG. 7 is a front perspective view thereof showing a medicine container adapted for connection thereto in exploded relation with respect the apparatus.

Protruding central portion 34 of outer shield 30 further includes an inlet port, generally referenced as 40, which functions as a receiving inlet for orally administered medications and/or the introduction of medical gases. In a preferred embodiment, inlet port 40 is defined by a cylindrical projecting wall 42 defining an interior volume bounded by a floor. The floor portion of inlet port 40 defines a plurality of apertures 44 providing fluid communication with chamber 20 via shaft bore 22. Inlet port 40 further includes a threaded peripheral edge 46 adapted for receiving a correspondingly threaded dispensing container 50 as best depicted in FIG. 7. Accordingly, measured doses of liquid medicine may provided to a patient directly to a location below the patient's tongue by attaching dispensing container 50 to inlet port 40 such that the liquid medicine flows through apertures 44 and shaft bore 22 into chamber 20 whereby the liquid medicine is allowed to exit chamber 20.

Figure 8:
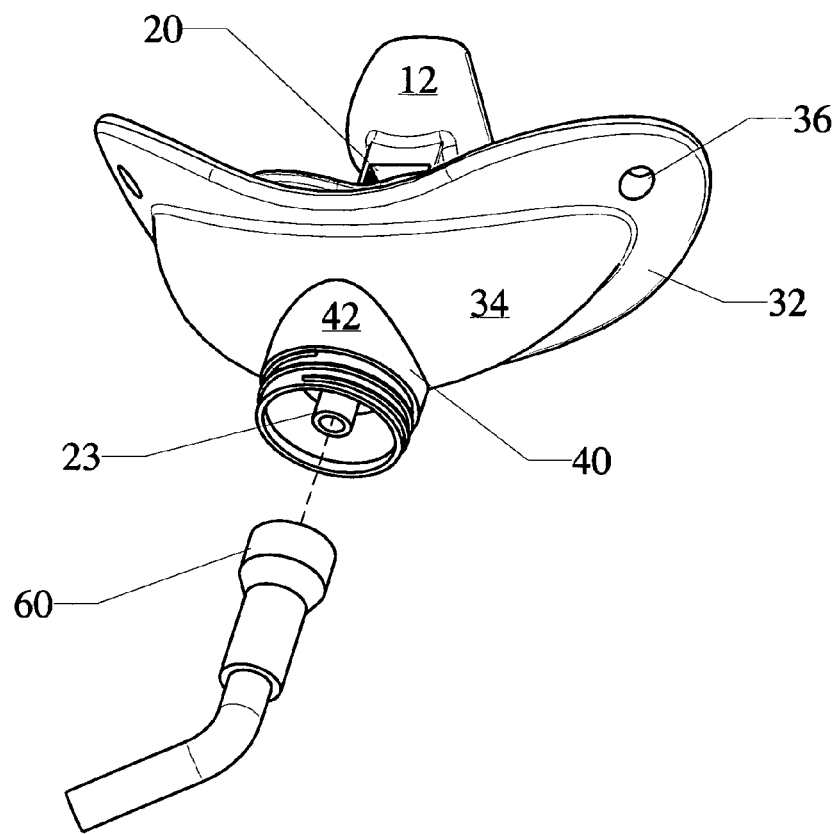
FIG. 8 is a front perspective view of the apparatus showing a fluid tube adapted for connection thereto in exploded relation with respect to the apparatus.

As best depicted in FIG. 8, shaft bore 22 includes a tubular end portion 23 that is axially disposed and terminates within inlet port 40. Tubular end portion 23 is adapted for mating engagement with a connector 60 to provide the user with a supply of medical gas, such as oxygen. Accordingly, oxygen or any other desired medical gas may be delivered to the user by attaching an oxygen supply hose 60 to the tubular end portion 23 such that oxygen flows through conduit 22 and out of chamber 20.

Figure 9:
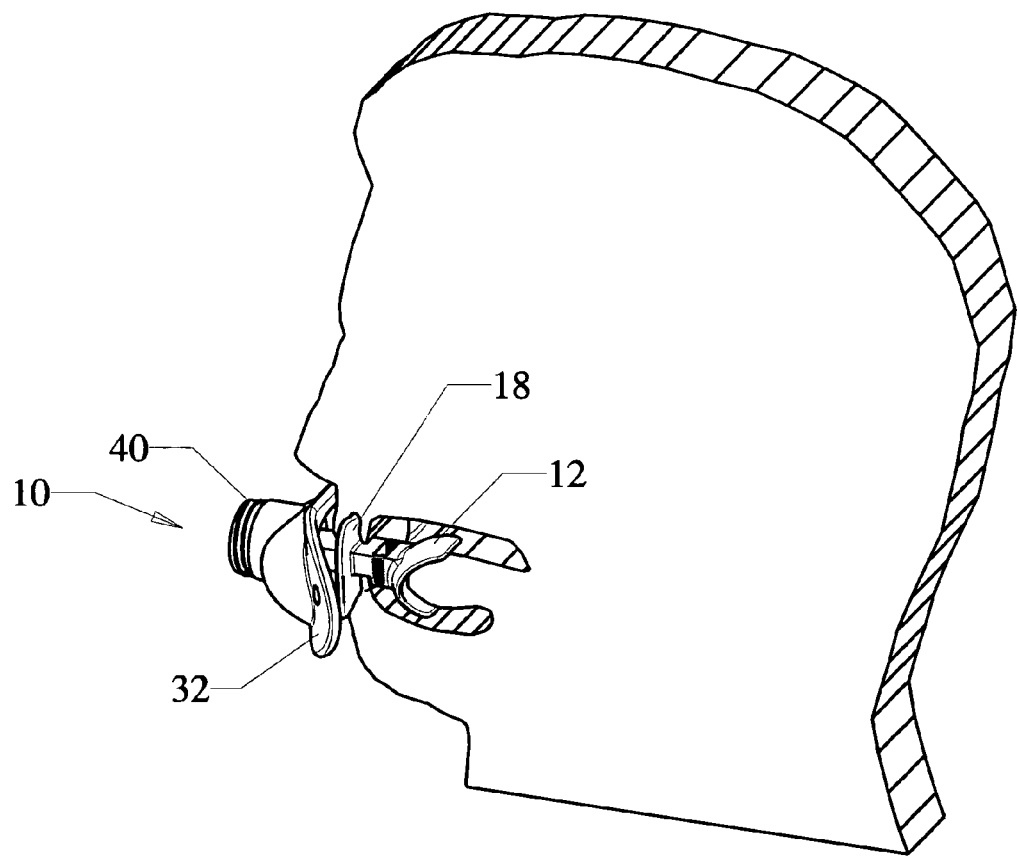
FIG. 9 is a perspective view illustrating the device relative to the oral cavity of a user when in use.

As best depicted in FIG. 9, the user inserts breathing normalizer 10 within the oral cavity in an operative configuration such that the tongue is received within tongue receiving structure 12, the teeth clamp down on connector 16 with the flanged lip plate positioned between the upper and lower teeth and the inner portions of the upper and lower lips. As a result of proper application of the apparatus breathing at night is normalized, while snoring, grinding of the teeth, and light sleep apena, are prevented.

The user may become accustomed to the device by wearing it for a few minutes before going to bed for a period of time. Once the user feels comfortable with the device, it may be worn in the mouth all night while sleeping. The duration of treatment depends on the severity of the abnormality and the condition of the tissues lining the oral cavity. It has been found, however, that use of the device for a period of some 15–20 days has proven successful in substantially reducing and/or eliminating breathing abnormalities, whereafter use of the device may be terminated. In the case of recurring breathing abnormalities, use of the device may recommence for a period of several nights.

Breathing normalizer 10 is used as follows:
1. Assigning

Breathing Normalizer is a small-sized preventive and treatment inside-mouth adaptor for personal use and is intended for preventing and treatment of breathing diseases, light forms of obstructive apnea syndrome (illness of apneas at sleep) and teeth grinding (grind of teeth at sleep) and, finally, will prolong the life of the patient.

2. Indication to application.

The application of the Breathing Normalizer is strongly recommended at following diseases: breathing dysfunctions, snore, light forms obstructive apnea syndrome and teeth grinding.

As a result of application of the Breathing Normalizer the steady medical effect is reached: (a) breathing at night is normalized; (b) quiet and able-bodied sleep is provided; (c) snore, apnea and grind of teeth at sleep are prevented and are completely eliminated; (d) enrichment of a blood by oxygen is increased and the metabolism processes are normalized during sleep; (e) pressure-jumps at night are prevented; and (f) the risk of extension of cardiovascular complications is reduced.

3. Contraindication to application:

The application of the Breathing Normalizer counter indicatives at: (a) chronic violation of nose breathing owing to a pathology (trauma, neoplasm etc.); (b) acute contagions and feverish condition with the obscure diagnosis; (c) the fissile forms of tuberculosis mild; and (d) adenoids or increased tonsils that handicapping breathing. It is necessary to abstain from applications of the Breathing Normalizer at the period of strong rhinitis and expedient nasal cavities.

4. Application:

a. Before usage of the Breathing Normalizer with the purpose of habituation and fine adjustment it is recommended during 3–4 days set the Breathing Normalizer in an oral cavity on 15–20 min before going to bed. If necessary period of adaptation can be prolonged. After adaptation the Breathing Normalizer remains in a mouth for all night.

b. The duration of treatment depends on a degree of disease and condition of mild tissues of an oral cavity of the patient and is in average 15–20 days. In case of steady absence of breathing dysfunction, further Breathing Normalizer usage can be stopped. In the case of a breathing dysfunction relapse the Breathing Normalizer is applied as required within any period of time from several days to several months.

5. For an avoidance of dryness in a mouth, it is recommended before each application to wet the Breathing Normalizer with warm water.

6. The greatest efficiency of operating of the Breathing Normalizer is reached in a body lying position at sleep.

7. Hygienic requirements, maintenance and storage: (a) Before and after application wash the Breathing Normalizer with warm water with toilet soap or other antiseptic; (b) Store the Breathing Normalizer in closed hygienic personal container at room temperature, in a dry place, excepting hits of straight lines of sunrays or store it in open air in the bathroom.

The instant invention has been shown and described herein in what is considered to be the most practical and preferred embodiment. It is recognized, however, that departures may be made therefrom within the scope of the invention and that obvious structural and/or functional modifications will occur to a person skilled in the art.

What is claimed is:

1. An apparatus for placement within the mouth of a user, the mouth having an exterior portion terminating in upper and lower lips, a posterior portion, and upper and lower gums therebetween, each gum having teeth projecting therefrom, and a tongue, said apparatus comprising:

an outer shield including an inlet port;

an elongate shaft having a first end terminating in a generally concave tongue receiving surface, and a second end disposed within said outer shield inlet port;

said shaft having an inner plate disposed between said outer shield and said concave tongue receiving surface, said inner plate sized for insertion in the mouth between the teeth and the lips; and said shaft including means for receiving oral medications and means for dispensing oral medications directly under the user's tongue.

2. An apparatus according to claim 1 wherein said inlet port is defined by a generally cylindrical wall having a peripheral edge adapted for threaded engagement with a medicine-containing cap.

3. An apparatus according to claim 1 wherein said shaft first tubular end is adapted for fluid communication with a tubular hose for supplying medial gas to the user.

4. An apparatus for placement within the mouth of a user, the mouth having an exterior portion terminating in upper and lower lips, a posterior portion, and upper and lower gums therebetween, each gum having teeth projecting therefrom, and a tongue, said apparatus comprising:

an outer shield, said outer shield including an inlet port defined by a generally cylindrical projecting wall and a floor;

an elongate shaft having a first end spaced from said outer shield and a second end disposed within said inlet port cylindrical wall;

a generally concave tongue receiving surface, having upper and lower lobes, connected to said shaft first end and disposed generally perpendicular to said shaft with said upper lobe disposed above said shaft and said lower lobe disposed below said shaft;

said shaft having an inner plate disposed between said outer shield and said concave tongue receiving surface, said inner plate sized for insertion in the mouth between the teeth and the lips;

said shaft including means for receiving oral medications and dispensing said oral medications below the user's tongue.

5. An apparatus for placement within the mouth of a user according to claim 4, wherein said apparatus is fabricated from a medical grade polymer.

6. An apparatus for placement within the mouth of a user according to claim 5, wherein said polymer changes color as the temperature thereof changes to indicate whether the user's temperature is normal or elevated.

7. An apparatus for placement within the mouth of a user according to claim 5, wherein said polymer is flavored.

8. An apparatus for placement within the mouth of a user according to claim 4, wherein said at least one outlet disposed proximal said concave tongue receiving surface comprises a chamber adapted for receiving a dosage of medication in either solid or liquid from for dispersion below the user's tongue.

* * * * *